United States Patent

Maeda et al.

Patent Number: 5,100,854
Date of Patent: Mar. 31, 1992

[54] PHOSPHONIUM SALTS AND PROCESSES FOR PRODUCTION OF AND USES FOR THE SAME

[75] Inventors: Toshihiko Maeda; Yasuo Tokitoh; Noriaki Yoshimura, all of Kurashiki, Japan

[73] Assignee: Kuraray Co., Ltd., Kurashiki, Japan

[21] Appl. No.: 620,211

[22] Filed: Nov. 30, 1990

Related U.S. Application Data

[62] Division of Ser. No. 492,882, Mar. 13, 1990, Pat. No. 4,992,609, which is a division of Ser. No. 211,034, Jun. 24, 1988, Pat. No. 4,927,960.

Foreign Application Priority Data

Jun. 24, 1987 [JP] Japan .................. 62-158290

[51] Int. Cl.$^5$ ............................ B01J 31/00
[52] U.S. Cl. ................................ 502/164
[58] Field of Search ........................ 502/164

[56] References Cited

U.S. PATENT DOCUMENTS

| | | | |
|---|---|---|---|
| 3,792,101 | 2/1974 | Hattori et al. | 585/509 |
| 3,823,199 | 7/1974 | Wright | 585/509 |
| 4,367,305 | 3/1981 | Yoshimura et al. | 524/398 |
| 4,417,079 | 2/1982 | Yoshimura et al. | 568/903 |

OTHER PUBLICATIONS

Yamamoto et al., Organometallics, "Interaction of Palladium (O) Complexes with Allylic Acetates, Allylic Ethers, . . . ", vol. 5, 1559–1567, 1986.
CA vol 54; 22362, 1960.
CA vol. 58; 91206, 1963.

Primary Examiner—Patrick P. Garvin
Assistant Examiner—E. D. Irzinski
Attorney, Agent, or Firm—Oblon, Spivak, McClelland, Maier & Neustadt

[57] ABSTRACT

Novel phosphonium salts of the general formula

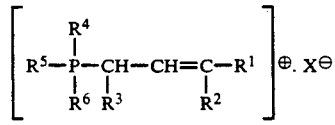

wherein $R^1$ and $R^2$ each is a hydrogen atom or a hydrocarbon group of 1 to 12 carbon atoms which may optionally be substituted; $R^3$ is a hydrogen atom or a hydrocarbon group of 1 to 5 carbon atoms which may optionally be substituted; $R^4$, $R^5$ and $R^6$ each is a hydrocarbon group of 1 to 8 carbon atoms which may optionally be substituted; X is a hydroxyl group, a hydroxycarbonyloxy group or a lower alkylcarbonyloxy group, and processes for production of the salts are described. Telomerization catalysts containing said phosphonium salts and processes for production of straight-chained alkadienyl compounds using the same catalysts are also provided.

5 Claims, No Drawings

PHOSPHONIUM SALTS AND PROCESSES FOR PRODUCTION OF AND USES FOR THE SAME

This is a division of application Ser. No. 07/492,882, filed on Mar. 13, 1990 now U.S. Pat. No. 4,992,609, which is a division of application Ser. No. 07/211,034, filed June 24, 1988, now U.S. Pat. No. 4,927,960.

BACKGROUND OF THE INVENTION

1. Field of the Invention

The present invention relates to novel phosphonium salts and processes for production of and uses for the same.

2. Description of the Related Art

Accounts of Chemical Research, 6, 8–15 (1973) and R. F. Heck, "Palladium Reagents in Organic Syntheses", pp.325–334, Academic Press, N.Y., 1985 describe that 1-substituted-2,7-alkadienes can be synthesized by subjecting a conjugated diene, such as butadiene, isoprene, etc., to telomerization reaction with an active hydrogen compound, such as water, alcohols, carboxylic acids, amines, ammonia, enamines, active methylene compounds, azides, silanes, etc., in the presence of a palladium catalyst and that favorable results can be obtained in the concomitant presence of a ligand such as triphenylphosphine in the reaction system.

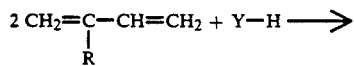

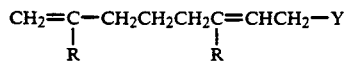

wherein R is a hydrogen atom or a methyl group; and Y is a group derived from an active hydrogen compound by removal of one active hydrogen atom.

As an example of the production of a 1-substituted-2,7-alkadiene compound by such telomerization reaction, there may be mentioned the production of 2,7-octadien-1-ol by telomerization reaction of butadiene with water as described in U.S. Pat. Nos. 3,670,032, 3,992,456, 4,142,060, 4,356,333 and 4,417,079, for instance.

It is generally acknowledged that in the telomerization reaction of a conjugated diene with an active hydrogen compound in the presence of a palladium catalyst, the use of a tertiary phosphorus compound, such as tri-substituted phosphines or tri-substituted phosphites, as a ligand is not only useful for modulating the reaction rate and reaction selectivity but also instrumental in stabilizing the catalyst. Therefore, as the catalyst for a telomerization reaction, it is common practice to use a low-valence palladium complex containing a ligand, such as a tri-substituted phosphine, or a chemical species prepared by reducing a palladium (II) compound in the presence of a ligand such as a tri-substituted phosphine. However, the following problems are involved in telomerization reactions using such catalysts. (1) The higher the concentration of the ligand, such as a phosphine compound, or the higher the molar ratio of the ligand to palladium, the higher is the stability of the palladium catalyst but the reaction rate is conversely decreased drastically (Chemical Communications, 1971, 330; etc.) and the higher the molar ratio of ligand to palladium, the lower is the selectivity of the reaction to a straight-chain alkadienyl compound, i.e. a compound derived by substitution of one or more active hydrogen atoms of an active hydrogen compound by 2,7-alkadienyl groups (Chemical Communications, 1971, 330; U.S. Pat. No. 3,992,456; etc.). Therefore, it is difficult to reconcile the requirements imposed by these two conflicting tendencies, i.e. stabilization of the palladium catalyst on the one hand and enhancement of high reaction rate and high selectivity to a straight-chain alkadienyl compound on the other hand. (2) The phosphine compound used as a ligand is liable to be oxidized in the presence of palladium [Angewandte Chemie International Edition in English, 6, 92–93, (1967)] and as the phosphine compound is recycled for telomerization reaction over a long time, there occurs an accumulation of its oxidation product, i.e. the phosphine oxide, but this phosphine oxide acts as a catalyst poison to exert adverse effects on telomerization (Japanese Patent Application Laid-Open KOKAI No. 4103/76). Incidentally, the phosphine oxide is hard to be separated and removed. (3) The research of the present inventors revealed that when a telomerization reaction is carried out using an excess of a phosphine compound relative to palladium, even if a low-valence palladium complex prepared from a palladium compound and a phosphine compound, the so-called active catalyst species, is used, the reaction involves a prolonged induction time. Particularly where the telomerization reaction is continuously conducted over a long period of time, more than a necessary amount of the palladium catalyst must be added, for the added catalyst cannot immediately exhibit its activity.

Since palladium is an expensive noble metal, it must be ensured in the use of a palladium catalyst in commercial production that the productivity per unit quantity of palladium be sufficiently high and the catalytic activity be sustained over a long time. From this point of view, it is of utmost importance to solve the aforesaid problems (1) to (3).

SUMMARY OF THE INVENTION

It is an object of the invention to provide a novel phosphonium salt which is of value as a component of the highly active catalyst for telomerization reaction.

It is another object of the invention to provide a process for producing said phosphonium salt.

It is a further object of the invention to provide a telomerization catalyst containing said phosphonium salt which has high activity.

It is still another object of the invention to provide a process for producing straight-chain alkadienyl compounds using said telomerization catalyst.

The present invention, in one aspect thereof, provides a phosphonium salt of the general formula

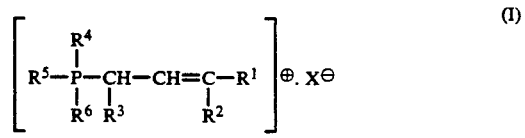

wherein $R^1$ and $R^2$ each is a hydrogen atom or a hydrocarbon group of 1 to 12 carbon atoms which may optionally be substituted; $R^3$ is a hydrogen atom or a hydrocarbon group of 1 to 5 carbon atoms which may optionally be substituted; $R^4$, $R^5$ and $R^6$ each is a hydrocarbon group of 1 to 8 carbon atoms which may optionally be substituted; X is a hydroxyl group, a hydroxycarbonyloxy group or a lower alkylcarbonyloxy group.

The present invention in another aspect provides a process for producing a phosphonium salt of general formula (I) characterized by reacting a tri-substituted phosphine of the general formula

  (II)

wherein $R^4$, $R^5$ and $R^6$ have the meanings defined hereinbefore, with at least one molar equivalent, relative to said tri-substituted phosphine, of an allylic compound of the general formula

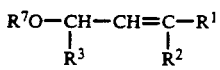  (III)

wherein $R^1$, $R^2$ and $R^3$ have the meanings defined hereinbefore; $R^7$ is a hydrogen atom or a lower alkylcarbonyl group, in the presence of a palladium compound in the presence or absence of water containing carbonate and/or hydrogen carbonate ion.

In a third aspect, the present invention provides a telomerization catalyst characterized by comprising a phosphonium salt of general formula (I) and a palladium compound.

In a fourth aspect, the present invention provides a process for producing a straight-chain alkadienyl compound which comprises reacting a conjugated diene with an active hydrogen compound in the presence of said telomerization catalyst.

DETAILED DESCRIPTION OF THE INVENTION

Referring to the above general formula (I), $R^1$, $R^2$, $R^3$, $R^4$, $R^5$, $R^6$ and X are further explained in detail below. The hydrocarbon group of 1 to 12 carbon atoms, independently represented by $R^1$ and $R^2$, is exemplified by aliphatic hydrocarbon groups such as alkyl groups, e.g. methyl, ethyl, n-propyl, n-butyl, n-pentyl, n-octyl, etc., and alkenyl groups, e.g. 2-propenyl, 3-butenyl, 4-pentenyl, etc.; alicyclic hydrocarbon groups such as cycloalkyl groups, e.g. cyclohexyl etc.; and aromatic hydrocarbon groups such as aryl groups, e.g. phenyl, tolyl, etc., and aralkyl groups e.g. benzyl and so on. The hydrocarbon group of 1 to 5 carbon atoms, represented by $R^3$, is exemplified by aliphatic hydrocarbon groups such as alkyl groups, e.g. methyl, ethyl, propyl, etc., and alkenyl groups, e.g. allyl, 4-pentenyl and so on. The hydrocarbon group of 1 to 8 carbon atoms, independently represented by $R^4$, $R^5$ and $R^6$, is exemplified by aliphatic hydrocarbon groups such as alkyl groups, e.g. methyl, ethyl, n-propyl, isopropyl, n-butyl, t-butyl, n-pentyl, n-octyl, etc.; alicyclic hydrocarbon groups such as cycloalkyl groups, e.g. cyclohexyl, methylcyclohexyl, etc.; and aromatic hydrocarbon groups such as aryl groups, e.g. phenyl, tolyl, etc., and aralkyl groups, e.g. benzyl and so on. The substituents which may be present on the hydrocarbon group represented independently by $R^1$, $R^2$, $R^3$, $R^4$, $R^5$ and $R^6$ include, among others, di(lower alkyl)amino groups such as dimethylamino etc.; a cyano group; and groups of the formula $-SO_3M$ or $-COOM$ (where M is an alkali metal atom such as lithium, sodium, potassium, etc.).

For use of the phosphonium salt of general formula (I) as a component of the catalyst for telomerization reaction, it is preferable in view of telomerization reaction data that at least one of $R^4$, $R^5$ and $R^6$ is an aryl group which is not substituted, such as phenyl, tolyl or the like, or an aryl group substituted by di(lower alkyl)amino, $-SO_3M$ or $-COOM$ (where M has the meaning defined hereinbefore),

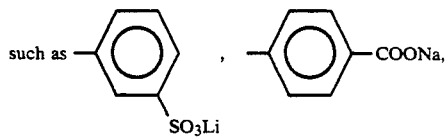

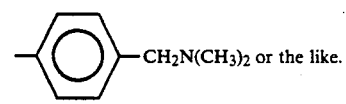

The lower alkylcarbonyloxy group represented by X is exemplified by acetoxy, propionyloxy, butyryloxy, isobutyryloxy, valeryloxy and so on.

The process for production of phosphonium salts of general formula (I) is described below.

The tri-substituted phosphine of general formula (II), which is used in the production of a phosphonium salt of general formula (I), is exemplified by aliphatic phosphines such as triisopropylphosphine, tri-n-butylphosphine, tri-t-butylphosphine, tri-n-octylphosphine, etc.; alicyclic phosphines such as tricyclohexylphosphine etc.; and aromatic phosphines such as triphenylphosphine, tritolylphosphine, diphenylisopropyl phosphine $(C_6H_5)_2PCH_2CH_2SO_3Na$, $(C_6H_5)_2PCH_2CH(CH_3)COONa$,

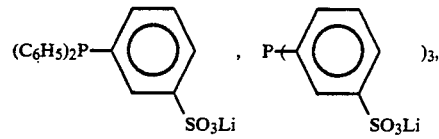

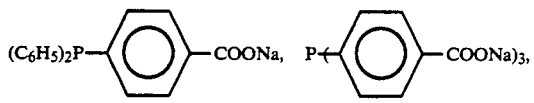

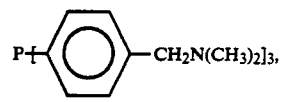

$(C_6H_5)_2PCH_2CH_2N(CH_3)_2$, $(C_6H_5)_2PCH_2COONa$ and so on. The lower alkylcarbonyl group, represented by $R^7$ in general formula (III), is exemplified by acetyl, propionyl, butyryl, isobutyryl, valeryl and so on. The allylic compound of general formula (III) is exemplified by allylic alcohols such as allyl alcohol, 2-methyl-2-propen-1-ol, 2-buten-1-ol, 2,5-hexadien-1-ol, 2,7-octadien-1-ol, 1,4-pentadien-3-ol, 1,7-octadien-3-ol, 2-octen-1-ol, etc.; and esters of such allylic alcohols with a carboxylic acid of the general formula $R^8OH$ (IV)

wherein $R^8$ is a lower alkylcarbonyl group, such as allyl acetate, 2-methyl-2-propenyl acetate, 2,5-hexadienyl acetate, 2,7-octadienyl acetate, 1-vinyl-5-hexenyl acetate, 1-vinyl-2-propenyl propionate, 2-octenyl propionate and so on. The amount of such allylic compound to be used in the production of a phosphonium salt of general formula (I) is not less than equimolar with respect to the trisubstituted phosphine. There is no critical upper limit to the amount of the allylic compound but in consideration of the ease of removal of the excess allylic compound after formation of the phosphonium salt of general formula (I), the allylic compound is preferably used in a proportion of about 1 to 10 moles per mole of the tri-substituted phosphine.

The palladium compound to be present in the reaction system for the production of a phosphonium salt of general formula (I) may be selected from among those palladium compounds which can be used generally for telomerization of conjugated dienes. As specific examples, there may be mentioned palladium (II) compounds such as palladium acetylacetonate, $\pi$-allylpalladium acetate, palladium acetate, palladium carbonate, palladium chloride, bisbenzonitrilepalladium chloride, etc. and palladium (0) compounds such as bis(1,5-cyclooctadiene)palladium, tris(dibenzylideneacetone)dipalladium and so on. Where a palladium (II) compound is used, there may be added a reducing agent for reduction of palladium (II) to palladium (O). The reducing agent used for this purpose is exemplified by alkali metal hydroxides such as sodium hydroxide etc., formic acid, sodium phenolate, $NaBH_4$, hydrazine, zinc powder, magnesium and so on. The preferred amount of the reducing agent may generally range from the stoichiometric amount required for reduction to about 10 times the amount. The amount of the palladium compound is such that there be made available 0.1 to 10 milligram-atoms, preferably 0.5 to 5 milligram-atoms of palladium per litter of the reaction mixture.

The reaction for the formation of a phosphonium salt of general formula (I) is carried out in the presence of the palladium compound and in the presence or absence of water containing carbonate ion and/or hydrogen carbonate ion. Where an allylic alcohol is used as the allylic compound, the reaction is generally conducted in the presence of water containing carbonate ion and/or hydrogen carbonate ion, whereby a phosphonium salt of general formula (I) wherein X is a hydroxyl group or a hydroxycarbonyloxy group is formed. When the ester of an allylic alcohol with a carboxylic acid of general formula (IV) is used as the allylic compound, the reaction can be conducted in the absence of said water containing carbonate ion and/or hydrogen carbonate ion, whereby a phosphonium salt of general formula (I) wherein X is a lower alkylcarbonyloxy group is produced. It is practically preferred that said carbonate ion and/or hydrogen carbonate ion be derived from carbon dioxide, a hydrogen carbonate such as sodium hydrogen carbonate, or a carbonate such as sodium carbonate within the reaction system. Among them, the ion derived from carbon dioxide is particularly desirable. Where carbon dioxide is used, a tertiary amine or quarternary ammonium hydroxide may be added for the purpose of increasing the carbonate ion concentration in the reaction system. The carbon dioxide partial pressure, where carbon dioxide is used, may range generally from 0 to 50 atmospheres (gage pressure) and, for practical purposes, is preferably in the range of 0 to 10 atmospheres (gage pressure).

The reaction for the formation of a phosphonium salt of general formula (I) may be conducted in the presence of an organic solvent which is inert to the reaction and is capable of dissolving the tri-substituted phosphine of general formula (II) and the allylic compound of general formula (III). Examples of such organic solvent include various ethers such as diethyl ether, dibutyl ether, tetrahydrofuran, dioxane, dioxolane, ethylene glycol dimethyl ether, polyethylene glycol dimethyl ether with an average molecular weight of 200 to 2,000, etc.; secondary or tertiary alcohols such as t-butanol, isopropyl alcohol, etc.; ketones such as acetone, methyl ethyl ketone, methyl isobutyl ketone, etc.; nitriles such as acetonitrile, benzonitrile, propionitrile, etc.; amides such as acetamide, propionamide, N,N-dimethylformamide, N,N-dimethylacetamide, etc.; sulfoxides such as dimethyl sulfoxide etc.; sulfones such as sulfolane, methylsulfolane, etc.; phosphoric acid amides such as hexamethylphosphoramide etc.; esters such as methyl acetate, ethyl acetate, methyl benzoate, ethylene carbonate, etc.; aromatic hydrocarbons such as benzene, toluene, xylene, ethylbenzene, etc.; and cyclic or acyclic aliphatic hydrocarbons such as butene, butane, hexane, cyclohexane, methylcyclohexane and so on. These solvents are generally used singly but may be used in combination as well.

The reaction for the formation of a phosphonium salt of general formula (I) is generally carried out at a temperature of 10° C. to 80° C. and, for practical purposes, preferably at room temperature. The reaction is generally carried through in 0.5 to 24 hours, and the endpoint of reaction can be easily ascertained by such a procedure as $^{31}$P-nuclear magnetic resonance spectrometry, liquid chromatography, iodometry or the like. As the atmosphere for the reaction, gases that do not adversely affect the reaction, such as carbon dioxide gas, nitrogen gas, etc., can be advantageously employed either singly or as a mixture.

The separation and purification of the phosphonium salt of general formula (I) from the resulting reaction mixture can be carried out by the following or other procedures. From the reaction mixture, the unreacted allylic compound and water, etc. are first distilled off under reduced pressure as necessary and the residue is washed with a solvent, such as methanol, diethyl ether, etc., to obtain crystals of the phosphonium salt of general formula (I).

The phosphonium salt of general formula (I), when used in combination with a palladium compound, gives a catalyst for use in the telomerization reaction of a conjugated diene with an active hydrogen compound. The amount of the phosphonium salt of general formula (I) as a component of this telomerization catalyst is generally at least 6 moles per gram-atom of palladium in the palladium compound, preferably 10 to 200 moles on the same basis, and for still better results, 30 to 100 moles on the same basis. The palladium compound as a component of said telomerization catalyst is any of the palladium (0) compounds or palladium (II) compounds which can be used in the reaction for the formation of a phosphonium salt of general formula (I). Where a palladium (II) compound is employed, the telomerization reaction can be conducted in the additional presence of a reducing agent. This reducing agent may be the same reducing agent as mentioned hereinbefore in connection with the reaction for the preparation of a phosphonium salt of general formula (I). The amount of the reducing agent is preferably in the range from the stoichiometric amount required for reduction to 10 times that amount. The telomerization catalyst comprising a phosphonium salt of general formula (I) and a palladium compound can be added to the telomerization reaction system by the following alternative procedures. Thus, the phosphonium salt and the palladium compound may be independently added or a mixture of the phosphonium salt and palladium compound may be added to the reaction system. An example of the latter method of addition is that the reaction mixture containing the phosphonium salt and palladium compound as obtained by the reaction for the formation of the phosphonium salt of general formula (I) is fed, either directly or after an appropriate workup procedure such as concentration or dilution, to the telomerization reaction system. The amount of the telomerization catalyst is such that the concentration of the palladium compound as a component of the catalyst is 0.1 to 10 milligram-atoms of palladium per liter of the telomerization reaction mixture and preferably 0.5 to 5 milligram-atoms on the same basis.

The conjugated diene to be used as a starting material in the telomerization reaction which is conducted with the aid of the above telomerization catalyst comprising a phosphonium salt of general formula (I) and a palladium compound may for example be butadine, isoprene or the like. The active hydrogen compound to be reacted with such a conjugated diene is a compound containing at least one reactive hydrogen atom, such as alcohols, phenols, amines, carboxylic acids, water, silanes, and active methyl, methylene or methine compounds activated by carbonyl, cyano, nitro, or the like. Among said alcohols are methanol, ethanol, butanol, allyl alcohol, 2-ethylhexanol, octadienol, stearyl alcohol, diethylene glycol, neopentyl glycol, pentaerythritol, trimethylolpropane, polyethylene glycol and so on. Among said phenols are phenol, cresol and so on. Said amines include ammonia, methylamine, dimethylamine, ethylamine, diethylamine, butylamine, morpholine, piperazine and so on. Among said carboxylic acids are acetic acid, propionic acid, adipic acid, benzoic acid, phthalic acid and so on. The silanes mentioned above are dimethylsilane, diethylsilane, dimethoxysilane and so on. Among said active methyl, methylene or methine compounds are methyl acetoacetate, acetylacetone, nitromethane, methyl cyanoacetate, ethyl 2-formyl-2-phenylacetate, 2-methyl-3-oxobutanenitrile, and so on.

In conducting the telomerization reaction, an additive may be used to increase the reaction rate. Examples of said additive include various bases such as alkali metal hydroxides, aliphatic tertiary amines, etc., salts of such bases with an acid which may for example be carbonic acid, phosphoric acid, acetic acid, boric acid or methanesulfonic acid, and weak acids such as boric acid, phosphorous acid, phenol and so on. Among these additives, one that is suited to the species of starting compound and other conditions is selectively used. For example, an increased reactivity of the active hydrogen compound can be expected by using an aliphatic tertiary amine as said additive when the active hydrogen compound is a carboxylic acid or by using the carbonate or hydrogen carbonate of an aliphatic tertiary amine when water is used as the active hydrogen compound.

The telomerization reaction can be conducted with the active hydrogen compound being utilized as a solvent as well but may likewise be conducted in the presence of an independent organic solvent that does not interfere with the reaction. As examples of such organic solvent, there may be mentioned those organic solvents which can, as aforesaid, be present in the reaction system for the formation of the phosphonium salt of general formula (I).

The telomerization reaction is carried out generally at a temperature of 40° C. to 100° C. and preferably in the range of 60° C. to 80° C. While such telomerization reaction can be conducted batchwise or continuously, a continuous process is preferable for commercial purposes.

By the telomerization reaction using the telomerization catalyst comprising a phosphonium salt of general formula (I) and a palladium compound, a straight-chain alkadienyl compound derived by substitution of one or more active hydrogen atoms of the active hydrogen compound by one or more 2,7-alkadienyl groups can be produced with high selectivity. The reaction product straight-chain alkadienyl compound can be separated from the catalyst component by a distillation process, for example using a film evaporator, or an extraction process such as the processes described in U.S. Pat. No. 4,356,333 and U.S. Pat. No. 4,417,079 but an extraction process is preferred in view of lower chances of deactivation of the catalyst component which make for recycling over an extended time. Thus, for example, where the telomerization reaction is carried out using water as the active hydrogen compound and a telomerization catalyst of this invention whose phosphonium salt component is a hydrophilic phosphonium salt containing a di(lower alkyl)amino group or a group of the formula —$SO_3M$ or —COOM (where M has the meaning defined hereinbefore) in an organic solvent having a high dielectric constant, such as sulfolane, ethylene carbonate, N,N-dimethylformamide or the like, extraction of the reaction mixture with a hydrocarbon such as hexane or the like gives the product compound in the extract and the catalyst component in the extraction residue.

The straight-chain alkadienyl compound thus obtained is useful as a synthetic intermediate for the production of n-octanol, n-octylamine, di-n-octyl phthalate, etc. or as a starting material for the manufacture of polymer modifying agents, perfumes, agricultural chemicals, drugs and so on.

According to the telomerization reaction using a telomerization catalyst comprising a phosphonium salt of general formula (I) and a palladium compound, not only is the straight-chain alkadienyl compound can be obtained with high selectivity but the reaction can be conducted substantially without an induction time and without formation of the oxidation product of the phosphine compound used which is known to be a catalyst poison. Furthermore, since this catalyst exhibits high activity, a sufficiently high reaction rate can be achieved even if the phosphonium salt of general formula (I) is used in large excess relative to the palladium compound for the purpose of improving the stability of the catalyst.

A further understanding of this invention can be obtained by reference to specific examples which are provided hereinbelow for purposes of illustration only and are not intended to be limitative of this invention.

EXAMPLE 1

Synthesis of a phosphonium salt

An autoclave equipped with a stirrer and carbon dioxide inlet and purging lines was charged with 30 ml of ion exchanged water, 110 ml of dioxane, 0.1 g of palladium acetate, 35 g of lithium diphenylphosphinobenzene-m-sulfonate and 25 g of 2,7-octadien-1-ol, and after the atmosphere in the autoclave was sufficiently purged with carbon dioxide gas, carbon dioxide gas was further introduced to establish a pressure of 5 kg/cm² (gage pressure). The temperature of the reaction mixture was increased to 60° C., at which temperature the reaction was conducted for about 20 hours. After completion of the reaction, the solvent was distilled off under reduced pressure and the solid residue was washed with 100 ml of ether and dried in vacuo at room temperature to recover 35 g of white powder.

Analysis of this white powder by high performance liquid chromatography [eluent: 0.01 mole/l aqueous phosphoric acid solution/methanol =1/4; column: YMC-Pack AM312 ODS (Yamamura Chemical Lab. Co., Ltd.)] showed no peak at the position of the starting material phosphine compound and a single peak at a different position. Based on results of elemental analysis for C and H and results of colorimetry for P, S and Li, the empirical formula of this compound was determined as $C_{27}H_{28}O_6SPLi$. To the white powder obtained above was added diluted (1N) sulfuric acid and the carbon dioxide gas evolved thereupon was quantitated by the barium hydroxide method. As a result, the molar ratio of atomic phosphorus contained in the white powder to the liberated carbon dioxide gas was found to be 1:1. Furthermore, using the above white powder, $^1H$— and $^{31}P$-NMR spectrometry and IR (infrared) absorption spectrometry were carried out. Based on results of these determinations, the white powder obtained as above was established to be a compound having the following structural formula.

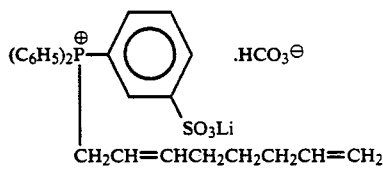

The $^1H$-NMR, IR and $^{31}P$-NMR spectrometric data on the product compound are shown below. $^1H$-NMR spectrum (in CDCl₃/, HMDS standard, 90 MHz, ppm). δ:1.00–1.33 (m, 2H) 1.63–2.10 (m, 2H) 4.06 (d of d, J=15 and 6.9 Hz. 2H) 4.66–6.00 (m, 5H) 7.31–7.96 (m, 12H) 7.96–8.40 (m, 2H).

IR spectrum (KBr disk, cm⁻¹) 690, 725, 755, 800, 970, 1040, 1110, 1210, 1230, 1400, 1440, 1485, 2940, 3410.

$^{31}P$-NMR spectrum (in 95% sulfolane-water (w/w), H₃PO₄ standard, ppm) δ: 21.55.

EXAMPLE 2

Synthesis of a phosphonium salt

An autoclave equipped with a stirrer, carbon dioxide inlet, sampling port, feeding port and purging line was charged with 100 g of 85% (by weight) tetrahydrofuran-water, 50 mg of palladium acetate and 3.16 g of triphenylphosphine and the mixture was stirred at a carbon dioxide pressure of 5 kg/cm² (gage pressure) for 30 minutes. Then, 3.5 g of allyl alcohol was fed and the reaction was conducted at an elevated temperature of 60° C. for 4 hours. After completion of the reaction, the solvent was distilled off under reduced pressure to obtain a solid residue. This solid was washed with 100 ml of ether and dried in vacuo to recover 2.9 g of white powder. Analysis of this powder by high performance liquid chromatography under the same operating conditions as in Example 1 showed no peak of triphenylphosphine but a single peak at a different position. Based on results of elemental analysis, colorimetry, quantitation of carbon dioxide gas, and $^1H$— and $^{31}P$-NMR spectrometric determinations, the above white powder was identified to be a compound having the following structural formula

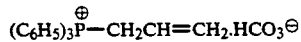

The $^1H$-NMR data on this compound are shown below.
$^1H$-NMR spectrum (in DMSO-d₆, HMDS standard, 90 MHz, ppm). δ:4.54 (d of d, J=15.6 and 6.6 Hz, 2H). 5.13–6.03 (m, 3H). 7.53–8.03 (m, 15H).

EXAMPLE 3

Synthesis of a phosphonium salt

The reaction and workup procedures of Example 1 were repeated except that 26 g of triphenylphosphine was used in lieu of 35 g of lithium diphenylphosphinobenzene-m-sulfonate to give 27 g of white powder. Analysis by high performance liquid chromatography revealed that it was a single compound different from triphenylphosphine. Furthermore, based on results of elemental analysis, colorimetry, quantitation of carbon dioxide gas, and $^1H$— and $^{31}P$-NMR spectrometric determinations, the structural formula of this compound was established as follows.

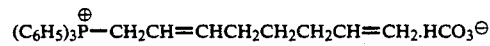

The $^1H$-NMR data on this compound are as follows.
$^1H$-NMR spectrum (CDCl₃, HMDS standard, 90 MHz, cm⁻¹). δ:1.05–1.48 (m, 2H). 1.63–2.08 (m, 4H). 4.05 (d of d, J=15 and 6 Hz, 2H) 4.63–5.91 (m, 5H). 7.32–7.93 (m, 15H).

EXAMPLE 4

Synthesis of a phosphonium salt

The reaction and workup procedures of Example 1 were repeated except that 40 g of sodium diphenylphosphinobenzene-m-sulfonate and 14 g of 2-buten-1-ol were used in lieu of 35 g of lithium diphenylphosphinobenzene-m-sulfonate and 25 g of 2,7-octadien-1-ol, respectively, to give 33 g of white powder. Analysis by high performance liquid chromatography revealed that this powder was a single compound different from the starting material phosphine compound. Furthermore, based on results of elemental analysis, colorimetry, quantitation of carbon dioxide gas, and $^1H$— and $^{31}P$-NMR spectrometric determinations, the structural formula of this product was determined as follows.

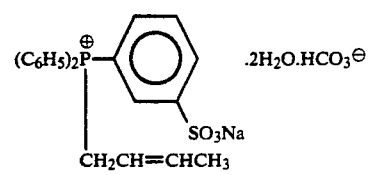

The $^1$H-NMR data on this product compound are shown below.

$^1$H-NMR spectrum (in DMSO-d$_6$, HMDS standard, 90 MHz, pm). δ: 1.40–1.65 (m, 3H). 4.38 (d of d, J=15.9 and 6.9 Hz, 2H). 5.00–5.93 (m, 2H). 7.47–8.10 (m, 14H)

EXAMPLE 5

Synthesis of a phosphonium salt

A three-necked flask fitted with a magnetic stirrer, carbon dioxide inlet and purging line was charged with 14 g of ion exchanged water and, then, carbon dioxide gas was bubbled into the water. Then, in the carbon dioxide gas atmosphere, 6.7 mg of palladium acetate and 0.42 g of lithium diphenylphosphinobenzene-m-sulfonate were fed to the flask. The mixture was stirred for about 30 minutes and 0.55 g of allyl alcohol was added using an injection syringe. While carbon dioxide gas was bubbled at atmospheric pressure and room temperature, the stirring was continued for about 4 hours. As a result, the reaction goes to completion, giving rise to a white precipitate. The precipitate was filtered through a glass filter and dried in vacuo to recover 0.40 g of white powder.

Analysis of this white powder by high performance liquid chromatography [eluent: 0.01 mole/1 aqueous phosphoric acid solution/methanol =¼, flow rate 1.2 ml/min; column: YMC-Pack AM312 ODS (Yamamura Chemical Lab. Co., Ltd.)] showed no peak at the position of the starting material lithium diphenylphosphinobenzene-m-sulfonate but a single peak at a different position. Furthermore, based on results of elemental analysis, colorimetry, quantitation of carbon dioxide gas, and IR absorption and $^1$H— and $^{31}$P-NMR spectrometric determinations, the structural formula of the above product was determined as follows.

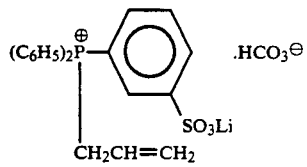

The $^1$H-NMR, IR and $^{31}$P-NMR data on the above product compound are given below.

$^1$H-NMR (DMSO-d$_6$, HMDS standard, 90 MHz, ppm). δ:4.58 (d of d, J=16.5 and 7.1 Hz, 2H). 5.14–6.00 (m, 3H). 7.57–8.16 (m, 14H).

IR absorption spectrum (KBr-disk, cm$^{-1}$) 690, 720, 760, 950, 1000, 1040, 1110, 1200 1240, 2940, 3430.

$^{31}$P-NMR spectrum (95% w/w sulfolane-water, H$_3$PO$_4$ standard, ppm). δ:21.35.

EXAMPLE 6

Synthesis of a phosphonium salt

A 300-ml three-necked flask fitted with a stirrer, cooling-condenser and thermometer was charged with 6.9 mg (0.031 mmole) of palladium acetate, 4.66 g (0.013 mole) of lithium diphenylphosphinobenzene-m-sulfonate, 3.5 g (0.021 mole) of 1-acetoxy-2,7-octadiene and 137 g of acetic acid in a nitrogen gas atmosphere and the mixture was refluxed for 4 hours. After completion of the reaction, the acetic acid was distilled off under reduced pressure using evaporator and the solid residue was washed with ether and dried to recover 7.15 g of powder. Analysis by high performance liquid chromatography revealed that this powder was a single compound different from the starting material phosphine compound. Furthermore, based on results of elemental analysis, colorimetry, and IR absorption spectrometric and $^1$H— and $^{31}$P-NMR spectrometric determinations, the structural formula of this product compound was determined to be as follows.

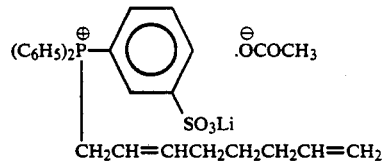

The $^{31}$P-NMR, $^1$H-NMR and IR data on the product compound are given below.

$^{31}$P-NMR spectrum (95% sulfolane-water, w/w). 21 ppm.

$^1$H-NMR spectrum (CDCl$_3$/HMDS). δ: 1.06–1.40 (2H). 1.60–2.20 (4H). 1.95 (s, 3H). 4.09 (d of d, J=15.2 and 7.2 Hz, 2H). 4.66–5.93 (m, 5H) 7.46–7.83 (m, 2H). 8.08–8.37 (m, 2H).

IR spectrum (KBr-disk, cm$^{-1}$). 665, 690, 720 (cis-olefin), 750, 800, 995 (trans-olefin), 1030, 1100, 1200 (—SO$_3$Li), 1400, 1570, 1710 (OAc$^\ominus$), 2850, 3010.

EXAMPLE 7

A 300-ml stainless steel autoclave equipped with an electromagnetic stirrer, carbon dioxide inlet, sampling port, feeding port, purging line and temperature controller was charged with 0.31 g (0.3 mmole) of tris(-dibenzylideneacetone)palladium, 6.2 g (12 mmole) of a phosphonium salt of the formula

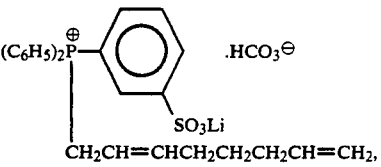

66 g of fully N$_2$-purged sulfolane, 68 g of water and 16.5 g of triethylamine in a nitrogen gas atmosphere. The reaction system was purged with carbon dioxide gas and the mixture was stirred at a carbon dioxide pressure of 5 kg/cm$^2$ (gage pressure) for 30 minutes. While the carbon dioxide partial pressure of the reaction system was maintained at 5 kg/cm$^2$ (gage pressure), the internal temperature of the system was increased to 75° C. and 40 ml of butadiene was fed in a single dose to initiate the reaction. After commencement of the reaction, a small amount of the reaction mixture was sampled at predetermined intervals and analyzed by gas chromatography. As a result, it was confirmed that the telomerization reaction proceeded without involving an induction period. Results of the analysis are set forth in Table 1.

TABLE 1

| | Reaction time (hrs.) | | | |
|---|---|---|---|---|
| | 1 | 1.5 | 2 | 3 |
| 2,7-Octadien-1-ol (mmoles) | 65.3 | 124.0 | 143.0 | 167.0 |
| 1,7-Octadien-3-ol (mmoles) | 3.3 | 6.8 | 7.5 | 8.9 |

TABLE 1-continued

| | Reaction time (hrs.) | | | |
|---|---|---|---|---|
| | 1 | 1.5 | 2 | 3 |
| Total (mmoles) | 68.6 | 130.8 | 150.5 | 175.9 |

Analysis of the catalyst solution after 3 hours of reaction revealed no formation of phosphine oxide and also showed that the palladium catalyst remained uniformly dissolved without precipitation of palladium metal.

EXAMPLE 8

The reaction procedure of Example 7 was repeated except that 4.37 g (12 mmoles) of a phosphonium salt of the formula

was used as the phosphonium salt and the reaction product was analyzed in the same manner as Example 7. The results are set forth in Table 2.

TABLE 2

| | Reaction time (hrs.) | | | |
|---|---|---|---|---|
| | 1 | 1.5 | 2 | 3 |
| 2,7-Octadien-1-ol (mmoles) | 63.0 | 119.6 | 139.3 | 162.1 |
| 1,7-Octadien-3-ol (mmoles) | 4.0 | 7.6 | 8.9 | 10.4 |
| Total (mmoles) | 67.0 | 127.2 | 148.2 | 172.5 |

EXAMPLES 9, 10 AND 11

The reaction procedure of Example 7 was repeated except that 12 mmoles each of the phosphonium salts mentioned in Table 3 were used as the phosphonium salts and the reaction products were analyzed as in Example 7. The results are set forth in Table 3.

addition of 50 ml of butadiene, and the reaction was conducted at 75° C. for 3 hours. The contents were then withdrawn and analyzed by gas chromatography. The analysis revealed that 1-acetoxy-2,7-octadiene and 3-acetoxy-1,7-octadiene had been produced in the amounts of 352 mmoles and 60 m moles, respectively.

EXAMPLE 13

The same reaction setup as used in Example 7 was charged with 50 g of sulfolane, 50 g of methanol, 2.16 g (5 mmoles) of a phosphonium salt of the formula $$(C_6H_5)_3\overset{\oplus}{P}-CH_2CH=CHCH_2CH_2CH_2CH=CH_2.HCO_3\ominus$$

and 0.2 g (0.2 mmole) of tris(dibenzylideneacetone)palladium in a nitrogen gas atmosphere. Then, 20 g of butadiene was added and the reaction was conducted at 75° C. for 1.5 hours. After completion of the reaction, the reaction mixture was analyzed by gas chromatography. The analysis revealed that 1-methoxy-2,7-octadiene and 3-methoxy-1,7-octadiene had been produced in the amounts of 17.7 g and 4.7 g, respectively.

From the above reaction mixture, the product compounds were separated by distillation at 75° C. in a vacuum of 25 mmHg using a film evaporator. The catalyst-containing sulfolane solution, obtained as a residue, was stirred in an open system exposed to air at room temperature for 24 hours. Analysis of the sulfolane solution after 24 hours of stirring revealed no formation of phosphine oxide. To this sulfolane solution were added 50 g of methanol and 20 g of butadiene and the mixture was reacted under the same conditions as in the first run. As a result, the reaction mixture contained 18.0 g of 1-methoxy-2,7-octadiene and 4.6 g of 3-methoxy-1,7-octadiene.

It is thus clear that the catalyst is highly stable against oxidation and still has high activity even after recovery from the reaction mixture.

TABLE 3

| | Example | | | | | |
|---|---|---|---|---|---|---|
| | 9 | | 10 | | 11 | |
| Phosphonium salt | $(C_6H_5)_3\overset{\oplus}{P}-CH_2CH=CH-$ $-CH_2CH_2CH_2CH=CH_2.HCO_3\ominus$ | | $(C_6H_5)_2\overset{\oplus}{P}-\underset{SO_3Na}{\bigcirc}.HCO_3\ominus$ $\underset{CH_2CH_2CH_2CH=CH_2}{CHCH=CH_2}$ | | $(C_6H_5)_2\overset{\oplus}{P}-\bigcirc-COONa$ $CH_2CH=CH_2 \quad .HCO_3\ominus$ | |
| Reaction time | | | Yield of NOD or IOD (mmoles) | | | |
| (hrs) | NOD | IOD | NOD | IOD | NOD | IOD |
| 1 | 63.3 | 4.2 | 58.5 | 3.0 | 60.7 | 3.1 |
| 2 | 120.0 | 7.9 | 135.5 | 6.8 | 133.0 | 7.0 |
| 3 | 139.5 | 9.1 | 150.3 | 8.0 | 155.3 | 8.3 |

(Note)
In the table, NOD stands for 2,7-octadien-1-ol and IOD stands for 1,7-octadien-3-ol.

EXAMPLE 12

The same reaction setup as used in Example 7 was charged with 60 g of acetic acid, 101 g of triethylamine, 4.6 g (12.6 mmoles) of a phosphonium salt of the formula

and 0.43 g (0.42 mmole) of tris(dibenzylideneacetone)palladium in a nitrogen gas atmosphere, followed by

EXAMPLE 14

The same reaction setup as used in Example 7 was charged with 67.8 mg (0.3 mmole) of palladium acetate, 6.2 g (12 mmoles) of a phosphonium salt of the formula

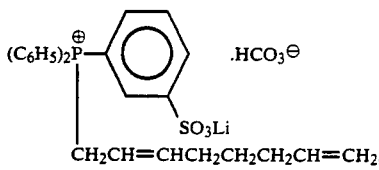

66 g of sulfolane, 68 g of water and 16.5 g of triethylamine. Then, with the internal pressure being maintained at 5 kg/cm² (gage pressure) using carbon dioxide gas, the temperature was increased to 60° C., and the mixture was stirred at 60° C. for 1 hour, after which the internal temperature was increased to 75° C. Then, 40 ml of butadiene was added in a single dose, whereupon the reaction started instantly. After 2 hours of reaction, the reaction mixture was analyzed by gas chromatography. The analysis revealed that 2,7-octadien-1-ol and 1,7-octadien-3-ol had been produced in the amounts of 49 mmoles and 7.5 mmoles, respectively.

EXAMPLE 15

The reaction procedure of Example 14 was repeated except that 12 mmoles of a phosphonium salt of the formula

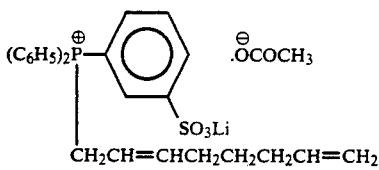

was used as the phosphonium salt and the reaction mixture was analyzed as in Example 14. As a result, the reaction mixture contained 153 mmoles of 2,7-octadien-1-ol and 9.1 mmoles of 1,7-octadien-3-ol.

EXAMPLE 16

The same reaction setup as used in Example 7 was charged with 17.8 mg (0.1 mmole) of palladium chloride, 2.28 g (4.3 mmoles) of a phosphonium salt of the formula

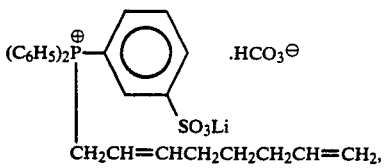

5 mg (0.11 mmole) of formic acid, 25 ml of triethylamine and 25 ml of acetic acid and the mixture was stirred in a nitrogen gas atmosphere at room temperature for 30 minutes. Then, 20 ml of butadiene was added and the reaction was conducted at 75° C. for 3 hours. As a result, 43 mmoles of 1-acetoxy-2,7-octadiene and 13 mmoles of 3-acetoxy-1,7-octadiene were produced.

COMPARATIVE EXAMPLE 1

The same reaction setup as used in Example 1 was charged with 70.0 g of 95 wt.% aqueous solution of sulfolane, 63.0 g of ion exchanged water, 16.5 g of triethylamine, 0.067 g of palladium acetate and 4.22 g of lithium diphenylphosphinobenzene-m-sulfonate, and carbon dioxide gas was introduced to establish a CO₂ partial pressure of 5 kg/cm² (gage pressure). The temperature was increased to 75° C. and 40 ml of butadiene was fed to initiate the reaction. After commencement of the reaction, the reaction mixture was sequentially analyzed by gas chromatography. As a result, an induction period of about 1 hour was found. After 3 hours of the reaction, the reaction mixture was analyzed by high performance liquid chromatography. The analysis showed a peak of phosphine oxide

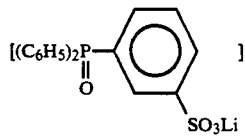

at a retention time of 4.0 minutes. Results of quantitative analysis of the products are given in Table 4.

TABLE 4

|  | Reaction time (hrs.) | | | |
|---|---|---|---|---|
|  | 1 | 1.5 | 2 | 3 |
| 2,7-Octadien-1-ol (mmoles) | 0 | 25.4 | 88.6 | 120.5 |
| 1,7-Octadien-3-ol (mmoles) | 0.2 | 8.8 | 10.0 | 12.1 |
| Total (mmoles) | 0.2 | 34.2 | 98.6 | 132.6 |

COMPARATIVE EXAMPLE 2

The same reaction setup as used in Example 7 was charged with 100 g of acetic acid, 20 g of triethylamine, 0.067 g of palladium acetate and 4.8 g of sodium diphenylphosphinobenzene-m-sulfonate in a nitrogen gas atmosphere. Then, 50 ml of butadiene was fed and the reaction was conducted at 75° C. for 3 hours. After 3 hours of reaction, the contents were withdrawn and analyzed by gas chromatography. The analysis revealed substantially no production of 1-acetoxy-2,7-octadiene or 3-acetoxy-1,7-octadiene. It is thus clear that the reaction rate is very low when the concentration of the phosphine compound is high.

COMPARATIVE EXAMPLE 3

In 100 ml of sulfolane were dissolved 0.23 g of tetrakistriphenylphosphinepalladium and 1.31 g of triphenylphosphine. The resulting sulfolane solution was stirred at room temperature in an open system exposed to air for 24 hours. As a result, 1.33 g of phosphine oxide was formed and palladium metal separated out.

COMPARATIVE EXAMPLE 4

The reaction procedure of Example 14 was repeated except that 12 mmoles of a phosphonium salt of the formula

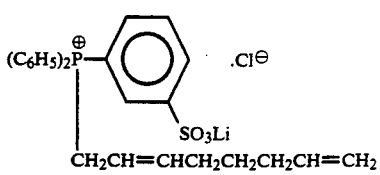

was used as the phosphonium salt and the reaction mixture was analyzed as in Example 14. It was found that the reaction had not progressed at all.

EXAMPLE 17

In this example, a total of 30 runs were carried out using the reactor and extraction apparatus described below.

Reactor: A 300-ml stainless steel autoclave equipped with a thermometer, stirrer, butadiene constant-feed pump, carbon dioxide gas inlet, liquid feeding port and liquid drain port was used as the reactor.

Extraction apparatus: A 800-ml pressure-resistant glass autoclave equipped with a thermometer, stirrer, gas inlet, n-hexane feeding port and liquid pressure feeding port was used as the extraction apparatus.

This extraction apparatus was directly coupled to the above reactor.

Method: The reactor was charged with 41 g of sulfolane, 45 g of distilled water, 14 g of triethylamine, 0.2 mg [corresponding to a concentration of 2 mmoles/l-charged reaction mixture] of trisdibenzylideneacetonepalladium, and 4.1 g of a phosphonium salt of the formula

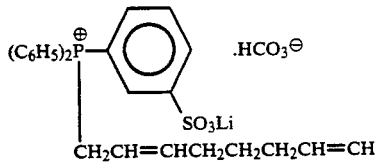

$CH_2CH=CHCH_2CH_2CH_2CH=CH_2$ and after the internal atmosphere was sufficiently purged with carbon dioxide gas, the mixture was heated to 70° C. with stirring and carbon dioxide gas was introduced to establish an internal pressure of 8 kg/cm$^2$ (gage pressure). Under stirring at 600 r.p.m., 15 ml of liquid butadiene was fed and the reaction was conducted at 75° C. for 60 minutes with a further continuous addition of butadiene at a rate of 14 ml/hr. The feeding of butadiene was stopped after 60 minutes of reaction and the reaction mixture was cooled and fed to the extraction apparatus by utilizing the pressure differential. After the extraction apparatus was pressurized to 3 kg/cm$^2$ (gage pressure) with carbon dioxide gas, 100 ml of n-hexane was added at 20° C. After 15 minutes of stirring, the reaction mixture was allowed to stand for 15 minutes for extraction with n-hexane. The upper layer (n-hexane layer) was withdrawn from the system by utilizing the pressure differential. To the residue was added 100 ml of n-hexane for re-extraction and the upper layer was withdrawn from the extraction system. The n-hexane layers were combined and analyzed by gas chromatography for the reaction product and sulfolane, by Karl-Fischer determination for water, titrimetry for triethylamine, and atomic absorption spectrometry and colorimetry for palladium and phosphorus (both on an atomic basis). The catalyst solution obtained as an extraction residue was supplemented with water in the amount equal to the sum of that consumed in the reaction and that extracted into the n-hexane layer, and triethylamine and sulfolane in the amounts equal to those extracted into the n-hexane layer, respectively, and fed back to the reactor by utilizing the pressure differential. Using the above catalyst solution, the series of reaction, extraction and catalyst recycling operations was repeated for a total of 30 runs. Throughout this series, no new addition of palladium and phosphorus components was made. The relation of the number of runs with reaction results and the amounts of palladium and phosphorus components extracted into the n-hexane layer is shown in Table 5. It is clear from Table 5 that the catalyst activity is maintained for a long time.

TABLE 5

| Number of runs | Octadienol (Note 1) | | Concentrations of catalyst components in n-hexane layer (ppm) | |
|---|---|---|---|---|
| | Yield (mmoles) | NOD/IOD mole ratio (Note 2) | Pd | P |
| 5 | 71 | 95/5 | 0.6 | 0.07 |
| 10 | 71 | 95/5 | 0.6 | 0.06 |
| 15 | 70 | 95/5 | 0.5 | 0.06 |
| 20 | 70 | 95/5 | 0.5 | 0.05 |
| 25 | 70 | 95/5 | 0.5 | 0.05 |
| 30 | 70 | 95/5 | 0.5 | 0.05 |

(Note 1) As products other than octadienols, 1,3,7-octatriene and dioctadienyl ether were detected and their yields were 1.2 to 1.3 mmoles for the former and 0.4 to 0.6 mmoles for the latter.
(Note 2) NOD stands for 2,7-octadien-1-ol and IOD stands for 1,7-octadien-3-ol.

EXAMPLE 18

The same reaction setup as used in Example 5 was charged with 70.0 g of 95 wt.% aqueous solution of sulfolane, 63.0 g of ion exchanged water, 16.5 g of triethylamine, 2.7 g of allyl alcohol, 67.4 mg of palladium acetate and 4.22 g of lithium diphenylphosphinobenzene-m-sulfonate and the reaction was conducted in a carbon dioxide gas atmosphere at room temperature for 5 hours to prepare a catalyst solution. Analysis of this catalyst solution by high performance liquid chromatography showed no peak of the starting material phosphine compound, indicating a completion of transformation.

An autoclave equipped with an electromagnetic stirrer, carbon dioxide gas inlet, sampling line, feeding line and purging line was charged with the whole amount of the above catalyst solution and carbon dioxide gas was introduced to establish a carbon dioxide partial pressure of 5 kg/cm$^2$ (gage pressure). Then, the temperature was set at 75° C. and 40 ml of butadiene was fed for telomerization reaction. After commencement of the reaction, the reaction mixture was sequentially analyzed by gas chromatography for the reaction products 2,7-octadien-1-ol and 1,7-octadien-3-ol. As a result, it was confirmed that the reaction had progressed without an induction period. Results of analysis by gas chromatography are shown in Table 6.

TABLE 6

| | Reaction time (hrs.) | | | |
|---|---|---|---|---|
| | 1 | 1.5 | 2 | 3 |
| 2,7-Octadien-1-ol (mmoles) | 64.5 | 122.0 | 142.0 | 165.0 |
| 1,7-Octadien-3-ol (mmoles) | 3.2 | 6.5 | 7.5 | 8.7 |
| Total (mmoles) | 67.7 | 128.5 | 149.5 | 173.7 |

Analysis of the catalyst solution by high performance liquid chromatography after 3 hours of reaction revealed no formation of phosphine oxide.

EXAMPLE 19

The same reaction setup as used in Example 5 was charged with 70.0 g of 95 wt.% aqueous solution of sulfolane, 20 g of ion exchanged water, 8.0 g of 2,7-octadien-1-ol, 67.3 mg of palladium acetate and 3.7 g of sodium 2-(diphenylphosphino)ethanesulfonate and the reaction was conducted in a carbon dioxide atmosphere at 50° C. for 10 hours to prepare a catalyst solution. Analysis of this catalyst solution by high performance liquid chromatography revealed no peak of the starting material phosphine compound, indicating a completion of transformation.

The same reactor as used in Example 18 for telomerization reaction was charged with 43 g of ion exchanged water and 16.5 g of triethylamine and carbon dioxide was bubbled into the mixture. Then, the whole amount of the above catalyst solution was fed and in the same manner as Example 18, the telomerization reaction was conducted and the reaction mixture was sequentially analyzed by gas chromatography. As a result, it was confirmed that the reaction had proceeded without an induction period. Results of gas chromatographic analysis are shown in Table 7.

TABLE 7

|  | Reaction time (hrs.) | | | |
| --- | --- | --- | --- | --- |
|  | 1 | 1.5 | 2 | 3 |
| 2,7-Octadien-1-ol (mmoles) | 48.2 | 94.8 | 115.5 | 146.9 |
| 1,7-Octadien-3-ol (mmoles) | 5.6 | 8.6 | 9.8 | 11.5 |
| Total (mmoles) | 53.8 | 103.4 | 125.3 | 158.4 |

Analysis of the catalyst solution by high performance chromatography after 3 hours of reaction revealed no formation of phosphine oxide.

EXAMPLE 20

A 50-milliliter three-necked flask was charged with 20 g of 95 wt.% aqueous solution of sulfolane, 5 g of ion exchanged water, 0.067 g of palladium acetate, 4.8 g of sodium diphenylphosphinobenzene-m-sulfonate and 1.4 g of allyl alcohol and while carbon dioxide gas was bubbled into the mixture, the reaction mixture was stirred at 50° C. for 4 hours. Analysis of the resulting catalyst solution by high performance liquid chromatography revealed no peak of the starting material phosphine compound, indicating a completion of transformation.

The same reaction setup as used for telomerization reaction in Example 18 was charged with 100 g of acetic acid, 20 g of triethylamine and the whole amount of the above catalyst solution in a nitrogen gas atmosphere. Then, 30 ml of butadiene was fed and the reaction was conducted at 80° C. for 3 hours. After 3 hours of reaction, the contents were withdrawn and analyzed by gas chromatography. The analysis revealed the formation of 1-acetoxy-2,7-octadiene and 3-acetoxy-1,7-octadiene in the yields of 52 mmoles and 15 mmoles, respectively. Analysis of the catalyst solution by high performance liquid chromatography after 3 hours of reaction showed no formation of phosphine oxide at all.

EXAMPLE 21

The same reaction setup as used in Example 7 was charged with 50 g of sulfolane, 0.2 g of 1-acetoxy-2,7-octadiene, 28 mg of palladium acetate and 0.17 g of di(n-butyl)phenylphosphine. The reaction was conducted at 50° C. for 2 hours to prepare a catalyst solution. Analysis of the catalyst solution by high performance liquid chromatography revealed no peak of the starting material phosphine compound, indicating a completion of transformation.

To the catalyst solution in the reaction setup were added 26 g of formic acid and 57 g of triethylamine and the mixture was stirred for 15 minutes. Then, 60 g of butadiene was added and the reaction was conducted at 70° C. for 2 hours. Analysis of the reaction mixture after 2 hours of reaction showed the formation of 48 g of 1,7-octadiene and 7.2 g of 1,6-octadiene.

What is claimed is:

1. A telomerization catalyst comprising a phosphonium salt of the general formula

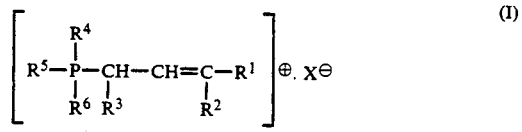

wherein $R^1$ and $R^2$ each is a hydrogen atom or a hydrocarbon group of 1 to 12 carbon atoms which may optionally be substituted; $R^3$ is a hydrogen atom or a hydrocarbon group of 1 to 5 carbon atoms which may optionally be substituted; $R^4$, $R^5$ and $R^6$ each is a hydrocarbon group of 1 to 8 carbon atoms which may optionally be substituted, at least one of $R^4$, $R^5$ and $R^6$ being an aryl group; X is a hydroxyl group, a hydroxycarbonyloxy group or a lower alkylcarbonyloxy group, the substituents of the substituted hydrocarbon group being di(lower alkyl) amino, cyano, —$SO_3M$ or —COOM, wherein M is an alkali metal, and a palladium compound.

2. The catalyst claimed in claim 1 wherein $R^1$ and $R^2$ in general formula (I) each is a hydrogen atom or an aliphatic hydrocarbon group of 1 to 12 carbon atoms and $R^3$ is a hydrogen atom or an aliphatic hydrocarbon group of 1 to 5 carbon atoms.

3. The catalyst claimed in claim 1 wherein $R^4$, $R^5$ and $R^6$ in general formula (I) each is an aryl group of 6 to 8 carbon atoms which may optionally be substituted by a group of the formula —$SO_3M$ (where M is an alkali metal atom).

4. The catalyst claimed in claim 1 wherein the proportion of the phosphonium salt is at least 6 moles per gram-atom of palladium in the palladium compound.

5. The catalyst claimed in claim 4 wherein the proportion of the phosphonium salt is in the range of 10 to 200 moles per gram-atom of palladium in the palladium compound.

* * * * *